United States Patent
Rajagopalan et al.

(10) Patent No.: US 8,377,694 B2
(45) Date of Patent: Feb. 19, 2013

(54) METHOD FOR THE CALIBRATION OF A DEVICE FOR MEASURING TOTAL ORGANIC CARBON CONTENT

(75) Inventors: Pascal Rajagopalan, Palaiseau (FR); Celine Le Ninivin-Glipa, Verneuil sur Seine (FR); Antony Vanheghe, Asnieres (FR)

(73) Assignee: EMD Millipore Corporation, Billerica, MA (US)

(*) Notice: Subject to any disclaimer, the term of this patent is extended or adjusted under 35 U.S.C. 154(b) by 61 days.

(21) Appl. No.: 12/897,122

(22) Filed: Oct. 4, 2010

(65) Prior Publication Data
US 2011/0244578 A1    Oct. 6, 2011

(30) Foreign Application Priority Data
Oct. 9, 2009   (FR) ..................... 09 57091

(51) Int. Cl.
*G01N 33/00* (2006.01)
*G01N 27/06* (2006.01)

(52) U.S. Cl. ............ 436/8; 436/146; 436/149; 436/150; 422/68.1; 422/78; 422/82.01; 422/82.02; 73/1.01; 73/1.02; 702/22; 702/23

(58) Field of Classification Search .............. 436/8, 133, 436/145, 146, 149, 150; 422/68.1, 78, 80, 422/82.01, 82.02; 73/1.01, 1.02; 702/22, 702/23
See application file for complete search history.

(56) References Cited

U.S. PATENT DOCUMENTS

| | | | | |
|---|---|---|---|---|
| 5,312,756 | A | * | 5/1994 | Jolly ................................. 436/8 |
| 5,340,542 | A | * | 8/1994 | Fabinski et al. ............ 422/82.05 |
| 6,228,325 | B1 | * | 5/2001 | Godec et al. .................... 422/80 |
| 6,447,725 | B1 | * | 9/2002 | Inoue et al. ..................... 422/80 |
| 6,451,613 | B1 | * | 9/2002 | Blades et al. ................ 436/146 |

(Continued)

FOREIGN PATENT DOCUMENTS

| | | |
|---|---|---|
| DE | 199 06 151 A1 | 9/2000 |
| DE | 10 2005 062 388 A1 | 6/2007 |

(Continued)

OTHER PUBLICATIONS

Ultrapure Water Journal, Nov. 9, 1998, XP-002585169; Robert P. Donovan et al.; "Evaluation of 3 Commercially Available, On-Line TOC Analyzers for Monitoring Recycled Water in Semiconductor Processing".

(Continued)

*Primary Examiner* — Maureen M. Wallenhorst
(74) *Attorney, Agent, or Firm* — Nields, Lemack & Frame, LLC

(57) ABSTRACT

A method for the calibration of a device for measuring the total organic carbon content (TOC) of an aqueous solution by measuring resistivity. The method includes the following steps, in the presence of a reference TOC analyzer: (a) producing a calibration point by a measurement carried out on ultrapure water by the device and the analyzer; (b) producing a plurality of calibration points, each calibration point corresponding to a measurement of the resistivity of a solution having a given content of photo-oxidizable compound, by the device and the analyzer, in order to establish a correlation between the values measured by the device and the analyzer; and (c) calibrating the device by at least one algorithm, based on the measurements carried out in the previous step.

18 Claims, 3 Drawing Sheets

U.S. PATENT DOCUMENTS

Figure 1:
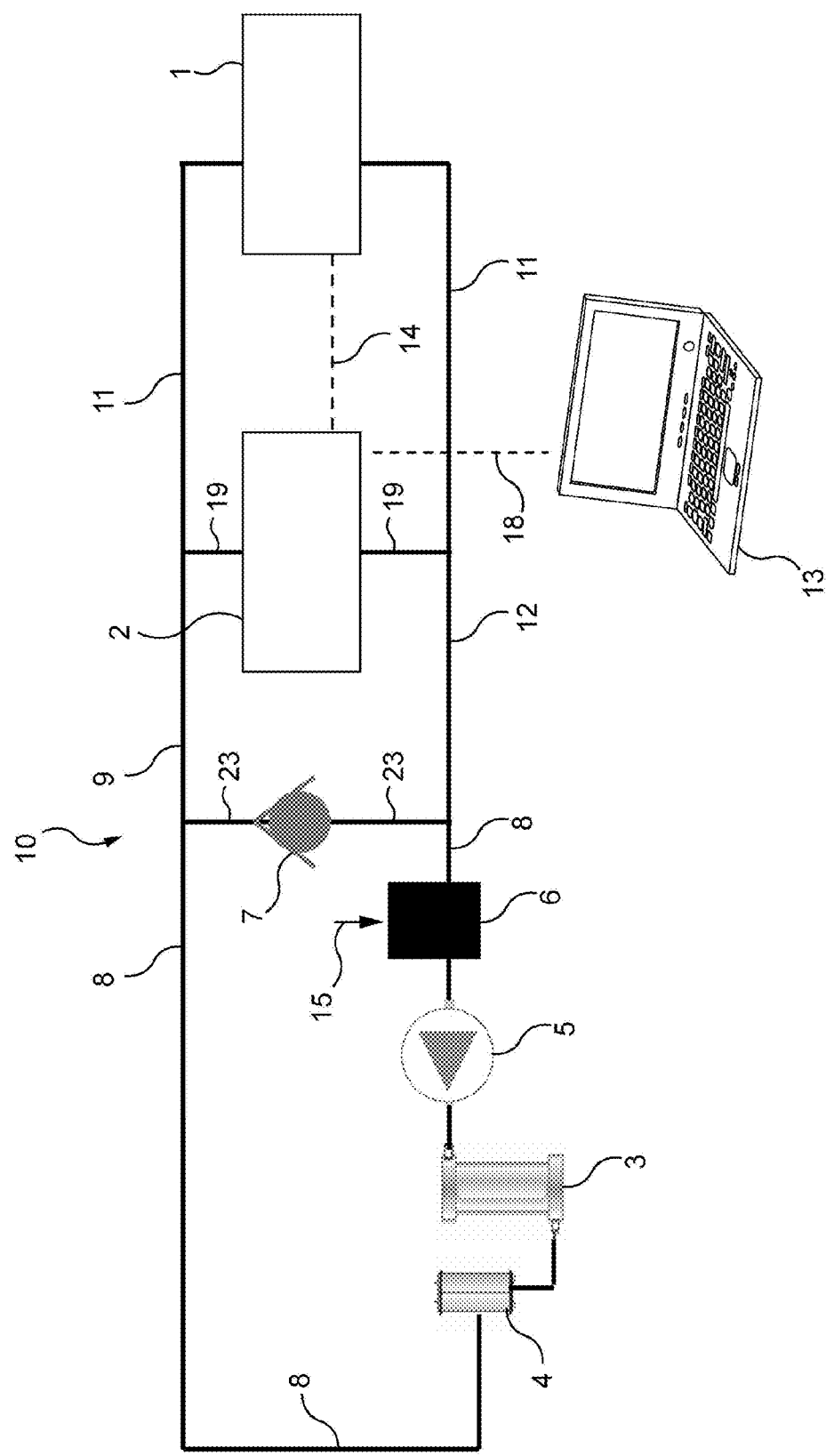

| | | | |
|---|---|---|---|
| 6,723,565 B2 * | 4/2004 | Davenport et al. | 436/133 |
| 2009/0145195 A1 | 6/2009 | Buttmann et al. | |
| 2010/0034702 A1 * | 2/2010 | Akechi et al. | 422/78 |
| 2010/0279417 A1 * | 11/2010 | Clay et al. | 436/52 |
| 2012/0039750 A1 * | 2/2012 | Yahata | 422/80 |

FOREIGN PATENT DOCUMENTS

WO          2007/053515      *     5/2007

OTHER PUBLICATIONS

French Search Report dated Jun. 2, 2010 in corresponding foreign application (FR0957091).

European Search Report dated Jan. 18, 2011 in corresponding European Patent Application No. 10290538, 4 pages.

European Communication dated Feb. 16, 2012 in corresponding European Patent Application No. 10290538, 4 pages.

Interphex West '96, SanDiego, CA, Session S-19, Nov. 1, 1996, XP55019148, 14 pages, "Calibration and Performance of a Conductivity System to Meet USP 23", [retrieved on Feb. 13, 2012], Bevilacqua.

"USP and International Pharmaceutical Water Requirements", May 1, 2002, XP55019141, 18 pages, [retrieved on Feb. 13, 2012], Bevilacqua.

General Electric, Water & Process Technologies, Analytical Instruments, 300 00123 Rev. A, MC-06-068, 2006, "A Science Based Performance Comparison of On-Line TOC Analyzers", pp. 1-17.

* cited by examiner

METHOD FOR THE CALIBRATION OF A DEVICE FOR MEASURING TOTAL ORGANIC CARBON CONTENT

The present patent application relates to the calibration of at least one device for measuring the total organic carbon (TOC) content of an aqueous solution, particularly ultrapure water.

Generally, measurement of the total organic carbon (TOC) content in aqueous solutions at low detection levels (i.e. a few tens or even a few hundreds of ppb) is carried out by a specific measurement device. In this device, a first step in the procedure is generally oxidation of the aqueous solution of which it is desired to measure the TOO content, usually in the presence of a source of UV radiation (for example at 185 nm), which leads to a conversion of the organic compounds to $CO_2$. This first step can also be carried out by photo catalysis or by another ozone generation method. It is followed by a second step of detecting the $CO_2$ molecules, usually by measuring resistivity (or conductivity) generally coupled with a temperature measurement. The complete oxidation of the first step is detected by a modification in the conductivity measurement taken by electrodes, coupled with the implementation of a complex set of algorithms. A processor (or Central Processing Unit (CPU)) controls the set of detectors and carries out the appropriate calculations. This makes it possible to obtain a measurement of the TOO content as a function of the resistivity value measured at the end of oxidation.

These measurement devices must be calibrated (i.e. standardized) regularly, typically at a frequency of once a year. In the state of the art, calibration of the resistivity is usually carried out by two measurements, one in the presence of ultra-pure water, which establishes a resistivity at 18.2 MΩ·cm for a TOC equivalent value of zero, and the other in the presence of water saturated with $CO_2$, which establishes a resistivity at 1 MΩ·cm for a TOC equivalent value of 200 ppb. This makes it possible to plot a linear calibration curve. A comparison with respect to a reference TOC analyzer, usually in the presence of a solution of methanol at 200 ppb, allows this calibration method to be checked.

The problems posed by this calibration method are, on the one hand, the assumed linearity of the calibration curve, and on the other hand, the limitation to a range of 0 to 200 ppb in TOC content, which is extrapolated up to 500 ppb without a high degree of reliability. However standards, in particular in the pharmaceutical industry, impose a measurement of the TOC content that is as reliable as possible up to a value of 500 ppb. The extrapolation according to the state of the art, for TOC values of 200 to 500 ppb, is not sufficiently reliable to be acceptable.

Moreover, in practice, a problem arises from the fact that the calibration solutions available on the market do not include a solution of water having a resistivity less than 18.2 MΩ·cm. Similarly, a solution of an easily photo-oxidizable organic compound, such as an alcohol, having a low concentration in said compound, is easily polluted by $CO_2$ in the air, notably reducing the reliability of any TOC content of this solution.

Finally, the necessity of handling gaseous $CO_2$ and managing its dissolution in pure water prevents this calibration method from being adapted for on-site use. In fact, using this method is tricky, and the equipment is relatively bulky. As a result, this method can prove complex to implement and inflexible in use.

The present patent application aims to remedy the drawbacks of the prior art, and in particular to implement a calibration method which does not have the drawbacks of the prior art.

To this end, the invention relates to a method for the calibration of at least one device for measuring the total organic carbon (TOC) content of an aqueous solution, in particular ultra-pure water, by measuring the resistivity of said solution at a given temperature, after oxidation of the carbon that it contains to $CO_2$, said method comprising at least the following series of steps, in the presence of a reference TOC analyzer:

(a) Producing a calibration point by measuring the resistivity of the ultra-pure water using the measurement device and the TOC analyzer, the resistivity having an established value equal to 18.2 MΩ·cm for a TOC equivalent value of zero, (b) Producing a plurality of calibration points, each calibration point corresponding to a measurement of the resistivity of a solution of a photo-oxidizable compound in ultra-pure water, having a given content of photo-oxidizable compound, generally of 0 to 500 ppb, said solution of photo-oxidizable compound having been oxidized, resistivity measurements being carried out by the measurement device and by the TOC analyzer, these calibration points making it possible to establish a correlation between the resistivity values measured by the TOC measurement device and those measured by the TOC analyzer; and (c) Correcting for the purposes of calibration of the TOC measurement device by at least one algorithm, on the basis of the measurements carried out in the previous step.

Advantageously, this method can be used on site.

The photo-oxidizable solution must generally be completely oxidized.

On the other hand, use of a calibration curve constructed on the basis of a plurality of points, makes it possible to appreciably improve the quality of the calibration method, in particular in the range of 0 to 200 ppb, but also in the range of 200 to 500 ppb.

Advantageously according to the invention, it is possible to carry out a calibration for a TOC content of 0 to 1000 ppb, preferably of 0 to 500 ppb, more preferably 2 to 500 ppb, even more preferably 3 to 500 ppb. For example, it is possible to carry out a calibration for a value of 0 to 200 ppb. This advantageously makes it possible to increase the reliability of the measurements of TOC content by the measurement device calibrated according to the method of the invention, quite particularly in the range of 200 to 500 ppb, but also of 2 to 500 ppb, or even of 3 to 500 ppb.

According to the invention, by ultra-pure water is meant a water which essentially only contains $H_2O$ molecules and $H^+$ and $OH^-$ in equilibrium (by autoprotolysis of the water), at a concentration of $10^{-7}$ mol/L at 25° C. Such water is generally used in the electronics industry and the pharmaceutical industry.

Preferably, the method according to the invention comprises a step (d) following step (c), said step (d) being a step of checking the TOC content measured by the measurement device in the presence of an aqueous solution of an organic compound having a given TOC content, generally comprised in the range of 0 to 500 ppb.

The compound of step (b) is photo-oxidizable under the conditions of implementation of step (b), as known to a person skilled in the art. It can also be described as "easily photo-oxidizable". In an embodiment of the invention, the compound of step (b) is chosen from alcohols and sucrose, preferably said compound is methanol or ethanol, and even more preferably said compound is methanol.

According to the method of the invention, simultaneous calibration of at least two different TOC measurement devices can be carried out. In this case, a second device is generally placed in parallel with the first device, on a by-pass of a fluid circulation loop passing through the first device. A similar procedure is used for any other additional device.

According to a variant of the invention, the step (c) comprises the use of at least one algorithm which carries out a comparison between the resistivity values of the TOC analyzer and those measured by the TOC measurement device, for each given TOC value, followed by the use of at least one algorithm which restores the resistivity values of the TOC measurement device as a function of the reference resistivity values provided by the TOC analyzer.

The oxidation is produced preferably using at least one source of UV radiation, the UV radiation source operating within a range of 120 to 400 nm, for example at 185 nm. But the oxidation can also be carried out by another oxidation technique: ozone, combustion, etc.

Preferably according to the invention, during step (b), a number of calibration points are produced, within a range of 5 to 35, preferably of 15 to 25, even more preferably of 18 to 22.

According to the invention, any solution can be circulated, the resistivity of which is measured within the measurement device and within the TOC analyzer, in the same fluid circulation loop. Generally this loop passes alternately or successively, preferably successively, through both of the devices. Preferably according to the invention said loop is equipped with at least one means of deionization or even decontamination, such as an ion-exchange resin and/or activated carbon.

The invention also relates to a calibration device for implementing a method as described previously. This device is generally such that it comprises at least one fluid circulation loop, at least one reference TOC analyzer, and at least one processor comprising at least one algorithm which carries out a comparison between the resistivity values of the TOC analyzer and those measured by the TOC measurement device for each given TOC value, and at least one algorithm which restores the resistivity values of the TOC measurement device as a function of the reference resistivity values provided by the TOC analyzer.

Such a device generally comprises at least one ion exchange resin cartridge, for example having polymer beads and/or activated carbon, which allows a deionized and/or decontaminated aqueous solution to be circulated.

Operation of the Calibration Algorithm

The processor of the device according to the invention generally comprises three modules; A, B and C.

Module A, which receives the measured TOC data from the reference analyzer and the measurement device to be calibrated, carries out the conversion of the TOC content to resistivity. These data can be raw resistivity values, or TOC values. The TOC data are firstly converted to equivalent resistivity. The reference TOC values and resistivity values can be provided by different reference devices. It should be noted that the present method operates whatever technology is used to measure the reference TOC unit (method of oxidation of organic matter by UV or by chemical route and method of detection by resistivity or by optical route, etc.) Thus in practice, the reference resistivity measurement can be carried out by a resistivity meter (Thornton Mettler Toledo trade mark, etc.) which generally provides a more accurate measurement than a resistivity cell incorporated into a TOC analyzer (Hach Ultra or GE Sievers trade mark).

Module A is based on the chemical equilibrium in the water of different chemical species ($CO_2$, $H^+$, $OH^-$, $HCO_3^-$, $CO_3^{2-}$, etc.). These equilibria are well known to a person skilled in the art. There are two hypotheses:

initially the water contains only organic molecules and ultrapure water, and is composed of the chemical elements C, H and O;

the sample is totally oxidized during the analysis by the unit under test.

According to these hypotheses, the conductivity of the totally oxidized sample is linked to the concentration of carbonate ions, from which the initial concentration of organic molecules is deduced.

Module B receives the resistivity data calculated by module A, as well as the resistivity data from the reference analyzer and the measurement device to be calibrated. Module B carries out the selection, or filtering, of the resistivity points, i.e. it filters the resistivity data provided by both apparatuses. The filtering is carried out as a function of the resistivity range measured. Points having too much noise (outliers, etc.) are also filtered. This module makes it possible to calculate an error linked to the uniform modelling over the whole operating range, for example by the least squares method, while avoiding any divergence from the polynomial modelled in module C below.

Module C relates to polynomial modelling, for example by the method of least squares. The polynomial is generally at least of order 2, typically of order 4. It therefore establishes the correlation between the values measured by the measurement device to be calibrated and those measured by the TOC analyzer. Subsequently, the module C provides calibration coefficients from a calibration resistivity table provided by module B.

Figure 2:
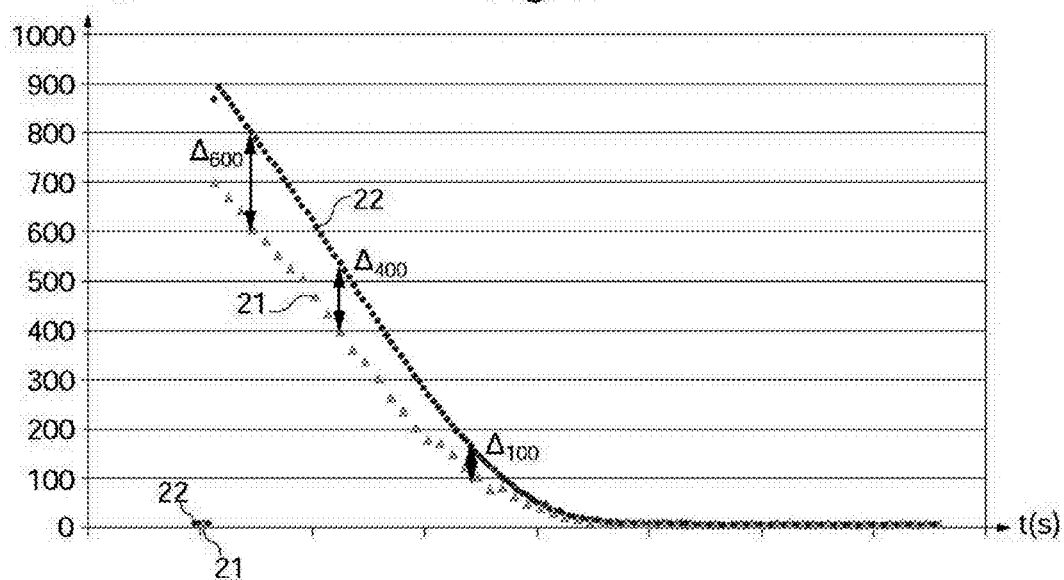
Figure 3:
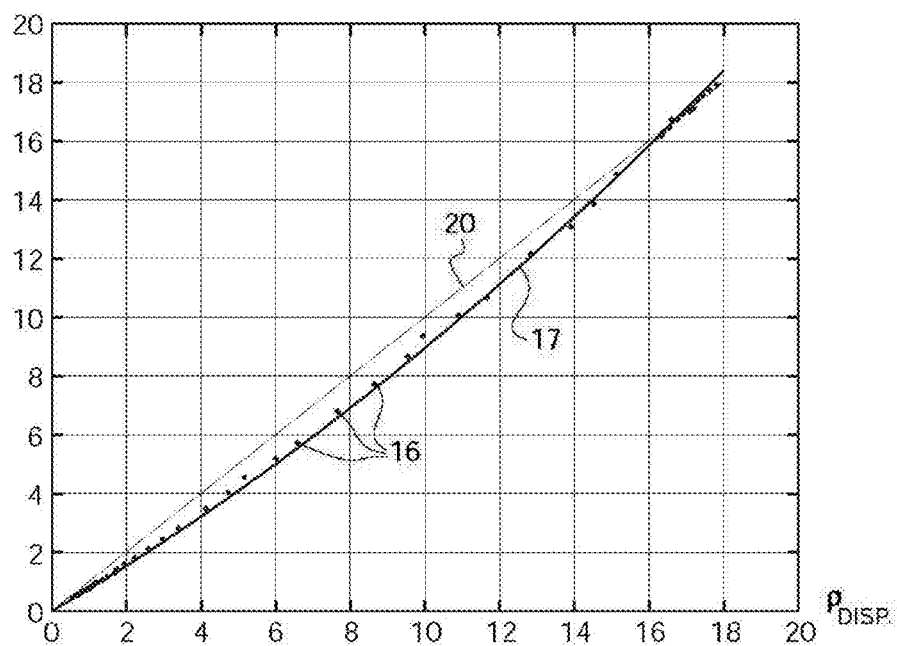
Figure 4:
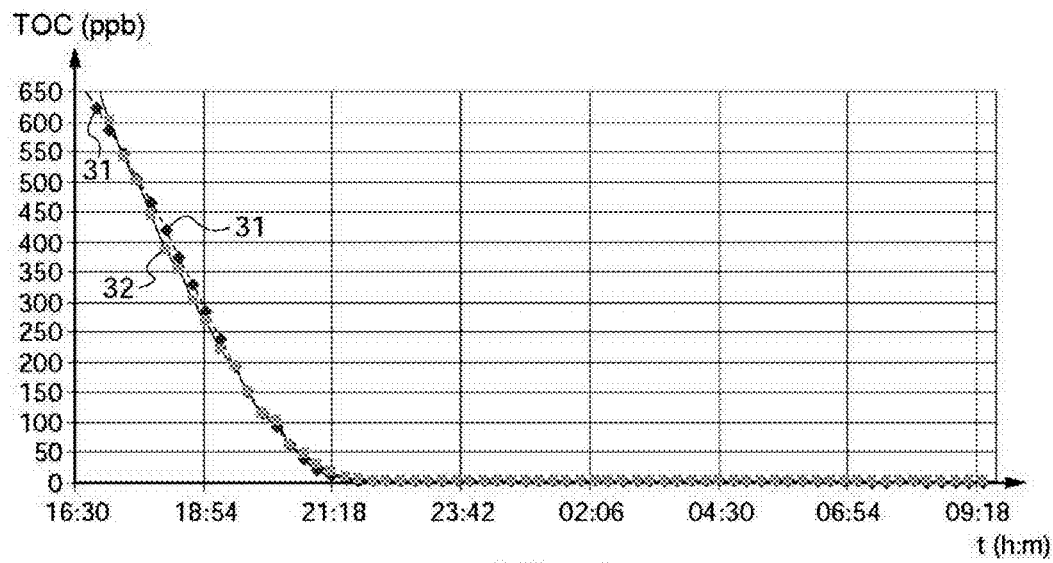
Figure 5:
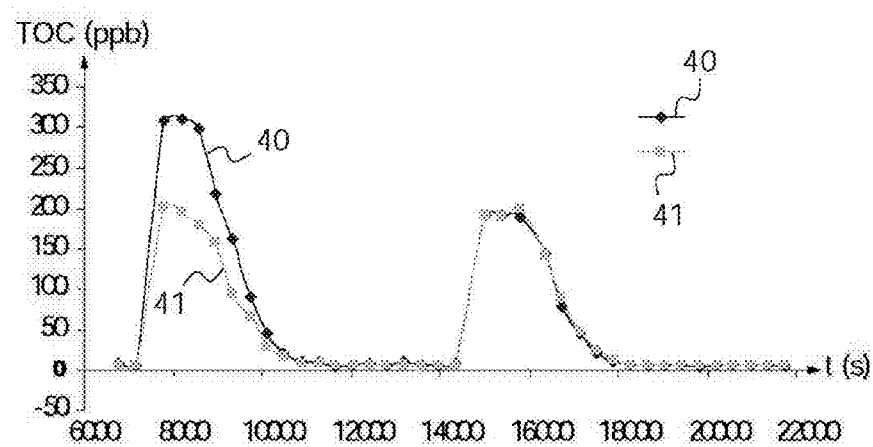

The invention will be better understood on reading the following figures, in which:

FIG. 1 diagrammatically represents a calibration device according to the invention;

FIG. 2 diagrammatically represents measurements of TOC content (ppb) as a function of time t (in seconds), by the device of FIG. 1 for implementation of the calibration method according to the invention, FIG. 3 diagrammatically represents a calibration curve obtained by implementation of the calibration method according to the invention, FIG. 4 diagrammatically represents measurements of TOC content (ppb) as a function of time t (in hours:minutes), by the device of FIG. 1 for checking this first implementation of the calibration method according to the invention, and FIG. 5 diagrammatically represents measurements of TOC content (ppb) as a function of time t (in seconds), a calibration curve obtained by a second implementation of the calibration method according to the invention.

FIG. 1 diagrammatically represents a calibration device 10 according to the invention.

This device 10 comprises a device 1 to be calibrated, for measuring the total organic carbon (TOC) content, as well as a reference TOC analyzer 2.

A pipe 11 passes through the device 1. A pipe 19 passes through the analyzer 2. The pipes 11 and 19 are fed by a pipe 9, itself fed by a pipe 8. The pipes 11 and 19 open into a pipe 12, which itself opens into the pipe 8. A by-pass pipe 23, which is located between the junction of pipes 8 and 9 and the junction of pipes 12 and 8, feeds a part 7 which is a non-return valve.

The non-return valve 7 allows an aqueous solution to circulate through the pipe 19, even during restriction of the flow of the solution in the pipes 11 and 19. This non-return valve 7 is generally calibrated, for example between 0.5 and 1 bar (or between 7 and 15 psi, i.e. in SI units between $5 \cdot 10^4$ Pa and $1 \cdot 10^5$ Pa).

The pipe 8 forms a closed loop with a reservoir 6. The reservoir 6 is itself fed by a feed device 15 which is either a syringe or a flask. Advantageously, this makes it possible to inject a concentrated solution which is diluted in the pipe 8. This concentrated solution is less likely to be polluted by the $CO_2$ of the air outside than an extremely dilute solution.

Starting from the reservoir 6, the pipe 8 passes through a pump 5, which allows any fluid present in the pipe 8 to be moved, a lamp 3 and a cartridge 4 capable of being filled with ion exchange resin beads. The lamp 3 is a UV lamp providing UV radiation capable of completely oxidizing the carbon present in an aqueous solution circulating in the circuit with dissolved $CO_2$.

The lamp 3 generally operates within a range of 185 to 254 nm, for example at 185 nm.

The cartridge 4 is generally capable of being filled with a mixed bed of two types of anionic and cationic beads, the beads being polymers, the bed optionally comprising moreover activated carbon intended to capture organic compounds, for example 10% by volume of activated carbon.

A dotted line 14 represents the possibility of wired or wireless data transmission between the measurement device 1 and the analyzer 2. A dotted line 18 represents the possibility of wired or wireless data transmission between the analyzer 2 and a processor present within a device 13 of the portable computer type.

In operation, an aqueous solution fed by the pipe 15 feeds the fluid circulation loop formed by the pipes 8, 9, 11, 19, 23 and 12. This feed is carried out via the reservoir 6 which regulates the circulation in the loop, in particular when it comprises an aqueous solution which must be substantially gas-free, apart from the $CO_2$ gas which can form by oxidation using the lamp 3. Said solution is generally either a flush solution or an aqueous solution with a predetermined TOC content.

This solution thus circulates within each of the two devices 1 and 2. A measurement of temperature and resistivity can be carried out in each of the two devices 1 and 2. This measurement is repeated many times, for example twenty times, on solutions having different TOC contents from 0 to 500 ppb or even 1000 ppb.

The processor of the device 13 receives the data from the two devices 1 and 2, and re-transmits data to these devices so as to modify the calibration of the measurement device 1. At the end of the calibration, the processor present in the device 13 can provide a calibration certificate.

Advantageously according to the invention, the device 10 is portable and can be taken on site.

EXAMPLES

Example 1

The following example was carried out using the device 10 as shown in FIG. 1, for which the UV lamp operated at 185 nm and 254 nm with a power of 17 W. The cartridge 4 contained approximately 1 L of resin of Millipore Quantum IX trade mark. The flow rate of the water was comprised between 20 and 100 L/h. The reference device was a TOC analyzer of Sievers 900RL (GE group) trade mark. The photo-oxidizable compound injected was high-purity methanol (HPLC type), at different concentrations.

FIG. 2 diagrammatically represents measurements of TOC content (in ppb) as a function of time t (in seconds, s).

The points 21, forming a curve 21, represent the set of calibration points measured by the measurement device 1, according to steps (a) and (b) of the first implementation of the method of the invention. One measurement of TOC content corresponds to one point. Similarly, the points 22, forming a curve 22, represent the set of calibration points measured by the reference TOC analyzer.

When the TOC content is measured by the device 1 equal to 100 ppb, 400 ppb or 600 ppb respectively, the difference on the y-axis between the curve 21 thus obtained and the curve 22 is $\Delta_{100}$, $\Delta_{400}$ or $\Delta_{600}$ respectively. The value of $\Delta_{100}$ is much smaller than the value of $\Delta_{400}$ which is itself much smaller than the value of $\Delta_{600}$. Thus, it can be seen in FIG. 2 that the difference in measurement at a given t, between curves 21 and 22 becomes greater as the TOC content (ppb) increases.

The differences between curves 21 and 22, in particular with high-content TOC measurements, especially above 200 ppb and even more above 500 ppb, are not acceptable as reliable measurements of the TOC content.

FIG. 3 diagrammatically represents a calibration curve 17 obtained by the first implementation of the calibration method according to the invention, based on points 16 taken from curves 21 and 22 in FIG. 2. This curve gives the reference resistivity measurement $\rho_{REF}$ of the reference TOC analyzer 2, with respect to the resistivity $\rho_{DISP}$ of the measurement device to be calibrated 1.

With respect to the straight line 20, the non-linearity of this calibration curve, which corresponds to actual values, can be seen.

The calibration according to the method of the invention is therefore particularly advantageous, in that it duly takes into account this absence of linearity.

FIG. 4 diagrammatically represents TOC contents (in ppb) as a function of time t (in hours:minutes, i.e. h:m) by the same device 10 of FIG. 1.

It makes it possible to check the calibration method according to the invention.

Thus, the curve 32 is the curve obtained with the reference analyzer 2, and the curve 31 is the curve obtained with the measurement device 1. It is noted that the two measurement curves are almost identical.

Example 2

A second example of implementation of the method of the invention was carried out using a device 10 as represented in FIG. 1, for which the UV lamp operated at 185 nm and at 254 nm with a power of 17 W. The cartridge 4 contained approximately 1 L of resin of Millipore Quantum IX trade mark. The flow rate of the water was comprised between 20 and 100 L/h. The reference device was a TOC analyzer of Sievers 900RL (GE group) trade mark. The photo-oxidizable compound injected was high-purity methanol (HPLC type), at different concentrations.

Table 1 below gives the measurements obtained, respectively for the device to be calibrated and for the reference analyzer, according to a first series of calibration measurements.

TABLE 1 raw data to be calibrated

| Device to be calibrated | | Reference analyzer | |
|---|---|---|---|
| TOC (ppb) | Temperature (° C.) | TOC (ppb) | Temperature (° C.) |
| 309.52 | 25.17 | 201.62 | 25.62 |
| 310.51 | 25.25 | 194.54 | 25.53 |
| 299.16 | 25.13 | 179.66 | 25.43 |
| 218.10 | 25.05 | 158.40 | 25.44 |
| 162.26 | 25.18 | 93.73 | 25.47 |
| 90.31 | 25.28 | 65.10 | 25.56 |
| 44.86 | 25.34 | 27.73 | 25.62 |
| 19.91 | 25.38 | 15.63 | 25.70 |
| 9.92 | 25.40 | 7.71 | 25.81 |
| 10.62 | 25.51 | 7.31 | 25.79 |
| 4.44 | 25.53 | 4.96 | 25.83 |

The calibration range is advantageously chosen completely independently of the standard existing TOC solutions.

According to the required precision in the given TOC ranges, it is possible to remove certain points from Table 1. United States Pharmacopeia Standard 643 requires a specific precision for a TOC analyzer of approximately 500 ppb. With the calibration method according to the invention, the points can be chosen around 500 ppb and at very low TOC values (<10 ppb) in order to adapt with the greatest precision to the standards for high and low TOC values in each situation.

The TOC values and the associated temperatures are processed in such a way as to produce a resistivity table (cf. Table 2 below) compensated to 25° C.:

TABLE 2 compensated resistivity data

| Resistivity of the device to be calibrated (Mohm · cm) | Reference resistivity (Mohm · cm) |
|---|---|
| 0.798 | 0.995 |
| 0.795 | 1.016 |
| 0.813 | 1.063 |
| 0.965 | 1.138 |
| 1.129 | 1.517 |
| 1.554 | 1.857 |
| 2.306 | 3.033 |
| 3.709 | 4.257 |
| 5.624 | 6.464 |
| 5.388 | 6.671 |
| 8.842 | 8.278 |
| 16.321 | 18.180 |

Although this is not obligatory, sampled resistivity values, such as the resistivity of ultra-pure water (18.2 Mohm·cm) could be included in Table 2. The calibration of the point at 18.2 Mohm·cm is equivalent to a theoretical value of 0 ppb.

The data of Table 2 are then processed in order to correspond to a polynomial calibration. A check is implemented in order to verify the new calibration coefficients (cf. Table 3).

TABLE 3

Verification of the TOC calibration

| Device to be calibrated TOC (ppb) | Reference analyzer0 TOC (ppb) |
|---|---|
| 191.73 | 191.98 |
| 191.04 | 189.38 |
| 189.82 | 199.15 |

TABLE 3-continued

Verification of the TOC calibration

| Device to be calibrated TOC (ppb) | Reference analyzer0 TOC (ppb) |
|---|---|
| 143.18 | 141.24 |
| 78.05 | 87.95 |
| 43.99 | 46.99 |
| 19.63 | 23.37 |
| 10.10 | 11.58 |
| 5.91 | 6.41 |
| 5.10 | 5.41 |

Relative or absolute deviations are defined according to the different TOC ranges. When all these criteria are approved by a given calibration device, the TOC certificate with the calibration and verification data is printed and provided to the owner of the device to be calibrated.

FIG. 5 shows a diagrammatic representation of measurements of the content of TOC (ppb) as a function of time t (in seconds) using this second implementation of the calibration method according to the invention according to Example 2: a first curve 41 for the values of the reference TOC analyzer and a second curve 40 for the device to be calibrated. The first part of these curves corresponds to the actual calibration, for values t comprised between approximately 6000 and approximately 11000 s, and a second part of these curves corresponds to the verification for values t comprised between 14000 and 18000 s.

The calibration method according to the invention therefore makes possible a reliable response to the need for precise calibration of TOC content from 0 to 500 ppb, or even from 0 to 1000 ppb.

The calibration method according to the invention thus shown according to the two previous examples of implementation has definite advantages in calibration of a device for the measurement of the total organic carbon (TOC) content of an aqueous solution, in terms of reliability, breadth of the range of values measured, simplicity and ease of use.

The invention claimed is:

1. Method for the calibration of at least one measurement device for measuring the total organic carbon (TOC) content of an aqueous solution containing carbon, by measuring the resistivity of said solution at a given temperature, after oxidation of the carbon that it contains to $CO_2$, said method comprising at least the following series of steps, in the presence of a reference TOC analyzer:

(a) Producing a calibration point by measuring the resistivity of ultra-pure water using said at least one measurement device and said TOC analyzer, the resistivity having an established value equal to 18.2 MΩ.cm for a TOC equivalent value of zero, (b) Producing a plurality of calibration points, the number of calibration points comprising 5 to 35, each calibration point corresponding to a measurement of the resistivity of a solution of a photo-oxidizable compound in ultra-pure water, having a given content of photo-oxidizable compound, said solution of photo-oxidizable compound having been oxidized, resistivity measurements being carried out by the measurement device and by the TOC analyzer, these calibration points establishing a correlation between the resistivity values measured by the TOC measurement device and those measured by the TOC analyzer; and (c) Correcting the TOC measurement device for calibration purposes by at least one algorithm, on the basis of the measurements carried out in the previous step, by using at least one algorithm which carries out a comparison between the resistivity values of the TOC analyzer and those measured by the TOC measurement device, for each given TOC value of a series of aqueous solutions having different TOC contents, followed by the use of at least one algorithm which restores the resistivity values of the TOC measurement device as a function of the reference resistivity values given by the TOC analyzer.

2. Method according to claim 1, further comprising a step (d) following the step (c), said step (d) comprising checking the TOC content measured by the measurement device in the presence of an aqueous solution of an organic compound having a given TOC content.

3. The method according to claim 2, wherein said TOC content is in the range of 0 to 500 ppb.

4. Method according to claim 1, wherein said photo-oxidizable compound is selected from the group consisting of alcohols and sucrose.

5. The method of claim 4, wherein said photo-oxidizable compound is methanol or ethanol.

6. The method of claim 4, wherein said photo-oxidizable compound is methanol.

7. Method according to claim 1, wherein the simultaneous calibration of at least two different TOC measurement devices is carried out.

8. Method according to claim 1, wherein the oxidation is produced using at least one source of UV radiation, the UV radiation source operating within a range of 120 to 400 nm.

9. Method according to claim 1, wherein a calibration is carried out for a TOC content of 0 to 1000 ppb.

10. Method according to claim 1, wherein any solution is circulated, the resistivity of which is measured within the measurement device and within the TOC analyzer, in the same fluid circulation loop.

11. Method according to claim 10, wherein said loop is equipped with at least one means of deionization or decontamination.

12. The method according to claim 1, wherein a calibration is carried out for a TOC content of 0 to 500 ppb.

13. The method according to claim 1, wherein a calibration is carried out for a TOC content of 2 to 500 ppb.

14. The method according to claim 1, wherein a calibration is carried out for a TOC content of 3 to 500 ppb.

15. The method of claim 1, wherein 15 to 25 calibration points are produced.

16. The method of claim 1, wherein 18 to 22 calibration points are produced.

17. Calibration device for calibrating at least one device for measuring the total organic content of an aqueous solution, said device comprising at least one fluid circulation loop, at least one reference TOC analyzer in said loop, a TOC measurement device in said loop, and at least one processor in communication with said at least one reference TOC analyzer and comprising at least one algorithm which carries out a comparison betweene resistivity values of the at least one TOC analyzer and those measured by said TOC measurement device for each given TOC value of a series of aqueous solutions having different TOC contents, and at least one algorithm which restores the resistivity values of the TOC measurement device as a function of the resistivity values given by the TOC analyzer, wherein said processor comprises three modules A, B and C, wherein module A receives the measured TOC data from the reference analyzer and the measurement device to be calibrated, and carries out the conversion of the TOC content to resistivity; module B receives the resistivity data calculated by Module A, as well as the resistivity data from said reference analyzer and said measurement device to be calibrated, and carries out the selection of the resistivity points as a function of the resistivity range measured; and module C establishes the correlation between the values measured by said measurement device to be calibrated and those measured by said TOC analyzer, and provides calibration coefficients from a calibration resistivity table proved by module B.

18. Device according to claim 17, comprising at least one cartridge of ion-exchange resin and/or activated carbon in said fluid circulation loop.

* * * * *

UNITED STATES PATENT AND TRADEMARK OFFICE
CERTIFICATE OF CORRECTION

PATENT NO. : 8,377,694 B2
APPLICATION NO. : 12/897122
DATED : February 19, 2013
INVENTOR(S) : Pascal Rajagopalan et al.

It is certified that error appears in the above-identified patent and that said Letters Patent is hereby corrected as shown below:

In the Claims

In column 10, Line 16, in Claim 17, delete "betweene" and insert -- between --, therefor.

In column 10, Line 26, in Claim 17, delete "resistivity;" and insert -- resistivity values; --, therefor.

In column 10, Line 27, in Claim 17, delete "data" and insert -- values --, therefor.

In column 10, Line 27, in Claim 17, delete "Module" and insert -- module --, therefor.

In column 10, Line 28, in Claim 17, delete "data" and insert -- values --, therefor.

In column 10, Line 35, in Claim 17, delete "proved" and insert -- provided --, therefor.

Signed and Sealed this
Twenty-fourth Day of September, 2013

Teresa Stanek Rea
*Deputy Director of the United States Patent and Trademark Office*